United States Patent [19]

Grynkewich

[11] 4,438,013
[45] Mar. 20, 1984

[54] PHOSPHORYLATED AND THIOPHOSPHORYLATED POLY(OXYALKYLATED) HYDRAZINES AND SELECTED ADDUCTS AND THEIR USE AS CORROSION INHIBITORS

[75] Inventor: Gregory W. Grynkewich, West Haven, Conn.

[73] Assignee: Olin Corporation, New Haven, Conn.

[21] Appl. No.: 499,039

[22] Filed: May 27, 1983

[51] Int. Cl.³ .................. C23G 1/06; C23G 1/18; C07F 9/02
[52] U.S. Cl. ................... 252/146; 252/78.5; 252/148; 252/149; 252/156; 252/174.16; 252/392; 252/541; 252/545; 252/389 R; 260/923
[58] Field of Search ............. 260/923; 252/78.5, 523, 252/142, 146, 148, 149, 541, 545, 174.16, 156, 389.2, 389.21, 392; 422/12, 13, 15

[56] References Cited

U.S. PATENT DOCUMENTS

| | | | |
|---|---|---|---|
| 2,878,189 | 3/1959 | Certa | 252/146 |
| 3,108,959 | 10/1963 | Klass et al. | 252/389.21 |
| 4,308,263 | 12/1981 | Oediger et al. | 260/923 |
| 4,317,741 | 3/1982 | Lederle et al. | 252/77 |
| 4,346,184 | 8/1982 | Drake | 252/389.2 |

FOREIGN PATENT DOCUMENTS 987354 3/1965 United Kingdom .

Primary Examiner—John E. Kittle
Assistant Examiner—Hoa Van Le
Attorney, Agent, or Firm—William A. Simons; Thomas P. O'Day

[57] ABSTRACT

Disclosed are compositions comprising the reaction products of poly(oxyalkylated) hydrazine and at least one compound selected from the group consisting of phosphorylation agents, thiophosphorylation agents, and mixtures thereof; wherein the poly(oxyalkylated) hydrazine has the formula:

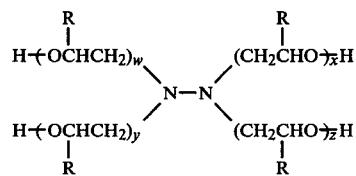

wherein each R is individually selected from hydrogen, lower alkyl groups having 1 to 4 carbon atoms, phenyl and mixtures thereof; the sum of w, x, y and z is from about 4 to about 25, and wherein the mole ratio of said poly(oxyalkylated) hydrazine to said compound being from about 0.1:1 to about 10:1. These compositions are shown to be effective corrosion inhibitors in corrosive aqueous solutions such as brines and acid metal-treating baths.

33 Claims, No Drawings

PHOSPHORYLATED AND THIOPHOSPHORYLATED POLY(OXYALKYLATED) HYDRAZINES AND SELECTED ADDUCTS AND THEIR USE AS CORROSION INHIBITORS

BACKGROUND OF THE INVENTION

1. Field Of The Invention

This invention relates to selected compositions which are the reaction products of poly(oxyalkylated) hydrazines and either phosphorylation agents or thiophosphorylation agents, or mixtures thereof. The present invention also relates to their use as corrosion inhibitors.

2. Brief Description Of The Prior Art

Poly(oxyalkylated) hydrazines are known compounds. For example, British Pat. No. 987,354, which issued to Farbenfabriken Bayer A. G. on Mar. 24, 1965, teaches that alkylene oxide adducts of hydrazine [e.g., tetra(hydroxypropyl)hydrazine] may be used to prepare cellular polyurethane.

U.S. Pat. No. 4,317,741, which issued to H. Lederle and F. Milnes on Mar. 2, 1982, teaches that selected poly(oxyalkylated) hydrazines are effective as corrosion inhibitors for hydraulic fluids. While these poly(oxyalkylated) hydrazines are good inhibitors for that use, they are not suitable for certain other aggressive environments such as aqueous acidic solutions, brines and sour brines. Accordingly, there is a need in the art to improve upon these poly(oxyalkylated) hydrazines so to make them more effective in other environments besides hydraulic fluids.

BRIEF SUMMARY OF THE INVENTION

The present invention is directed to, as compositions of matter, the reaction products of poly(oxyalkylated) hydrazine and at least one compound selected from the group consisting of phosphorylation agents, thiophosphorylation agents, and mixtures thereof, wherein said poly(oxyalkylated) hydrazine has a formula (I):

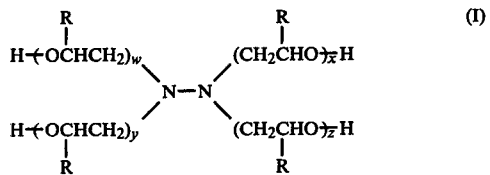

wherein each R is individually selected from hydrogen, lower alkyl groups having 1 to 4 carbon atoms and phenyl; and the sum of w, x, y, and z is from about 4 to about 25, and wherein the mole ratio of said poly(oxyalkylated) hydrazine to said compound being from about 0.1:1 to about 10:1.

The present invention is also directed to, as compositions of matter, substantially HCl-free reaction products of poly(oxyalkylated) hydrazines and either chlorine-containing phosphorylation agents (e.g. phosphoryl chloride-$POCl_3$) or chlorine-containing thiophosphorylation agents (e.g. thiophosphoryl chloride-$PSCl_3$).

The present invention is further directed to, as compositions of matter, adducts of an iodide-containing compound (e.g. HI) and the above-noted reaction products of poly(oxyalkylated) hydrazines and either phosphorylation agents, thiophosphorylation agents, or mixtures thereof. These iodide-containing reaction products may be either substantially HCl-free or contain HCl.

The present invention is still further directed to the use of these compositions as corrosion inhibitors.

DETAILED DESCRIPTION

The synthesis of the poly(oxyalkylated) hydrazines of the present invention is described in the above-noted U.S. Pat. No. 4,317,741. This U.S. Pat. is incorporated herein by reference in its entirety. Generally, these poly(oxyalkylated) adducts of hydrazine may be made by reacting one mole of hydrazine, either in anhydrous form or in an aqueous solution (such as hydrazine hydrate), with about four or more moles of either ethylene oxide (EO), propylene oxide (PO), butylene oxide (BO), styrene oxide (SO), or the like, or mixtures thereof (either sequentially or mixed together).

It should be understood that the number of moles of oxide reacted at each of the four reactive sites of the hydrazine molecule will not always be the same. For instance, if 12 moles of PO were reacted with one mole of hydrazine, it does not necessarily follow that 3 moles of PO will react at each site. Instead, it may be in some instances that only 1 mole or maybe none, will react at one site and 7, or more, moles may react at another site. Furthermore, it should be understood that the total number of alkylene oxide moles on each resulting adduct molecule will be statistically distributed. Thus, the sum of w, x, y, and z in Formula (I) represents the average number of alkylene oxide units per adduct and that the actual number of any given adduct may be less or greater than that sum. That is, when $w+x+y+z=12$, it is meant that 12 moles of an alkylene oxide like EO or PO have been reacted per mole of hydrazine.

Preferably, it is desired to employ from about 6 to 20 moles of alkylene oxide per mole of hydrazine. The preferred alkylene oxides are EO, PO, and mixtures thereof (either together or sequentially) because of cost considerations. Also preferably, all of these four reaction sites on the hydrazine molecule are reacted (i.e., each of w, x, y, and z are at least 1) in order to prevent undesirable side reactions. The covering of all four of the hydrazine reaction sites is better assured when at least about 6 moles of alkylene oxide are employed per mole of hydrazine.

The phosphorylation agents and thiophosphorylation agents used as the other reactants of the present invention generally are commercially available. Any conventionally known phosphorylation agent or thiophosphorylation agent may be employed. The preferred phosphorylation agents are phosphoryl chloride and phosphorus pentoxide because of cost and availability. Phosphoryl chloride is the most preferred because of ease of use. Likewise, the preferred thiphosphorylation agents are thiophosphoryl chloride and phosphorous pentasulfide because of cost and availability. Thiophosphoryl chloride is most preferred because of ease of use.

As stated above, mole ratios of the poly(oxyalkylated) hydrazine to the phosphorylation agent or thiophosphorylation agent from about 0.1:1 to about 10:1 are needed for desirable performance. More preferred are mole ratios from about 1:1 to about 6:1. Most preferred are mole ratios in the range from about 2:1 to about 5:1.

It should be noted that the reaction product of a poly(oxyalkylated) hydrazine and a phosphorylation agent or thiophosphorylation agent is not a single identifiable product, but a group of products. Thus, the reaction product cannot be identified explicitly and may be slightly different depending upon many factors such as reaction temperatures and times. It should be noted that HCl is a by-product of the reaction when either POCl$_3$ or PSCl$_3$ is employed.

Any conventional reaction conditions designed to react poly(oxyalkylated) hydrazines to either phosphorylation agents or thiophosphorylation agents may be employed in the synthesis of the present compounds and the present invention is not intended to be limited to any particular reaction condition. Advantageously and preferably, the present compositions may be made with or without an inert solvent. The reaction temperature and time will both depend upon many factors including the specific reactants and apparatus employed. In most situations, reaction temperatures from about 10° C. to about 120° C., preferably from about 20° C. to 100° C., may be employed for the main reaction period. Likewise, the post reaction temperature is not critical, but temperatures in the range from about 30° C. to about 130° C. are preferred. Temperatures from about 60° C. to about 90° C. are more preferred. Reaction times from about 30 minutes to 24 hours may be employed. Post-reaction heating times may vary from about 1 hour to 6 hours. The reaction is preferably carried out under atmospheric pressure; however, subatmospheric and superatmospheric pressure may be employed. The desired reaction product may be recovered from the reaction mixture by any conventional means.

It may be desired to remove substantially all or a portion of the HCl by-product formed during this reaction, which may be still attached to the reaction product. This may be done simply by passing an aqueous solution of the reaction product through an anion exchange resin where some or substantially all of the HCl groups will be removed without otherwise changing the character of the product. One suitable anion exhange resin is Amberlite IRA-400(OH) produced by the Rohm and Haas Company of Philadelphia, PA. Other equivalent resins may be employed.

It may also be desirable to combine an iodide-containing compound with the reaction product to enhance its corrosion-inhibiting properties for certain applications. This may be easily done by adding an iodide-containing compound such as HI to an aqueous solution of the reaction mixture and then removing the water. The amount of iodide added is not critical to the present invention. It is preferred to add sufficient amounts of iodide-containing compound so that the final content of the resulting adduct will be from about 0.5% to about 20%. The water used as a solvent for making these adducts may be removed by any conventional means, such as vacuum stripping.

Also, in accordance with the present invention, it has been found that the compounds of Formula (I), above, may be utilized as effective corrosion inhibitors. In practicing the process of the present invention, metal surfaces are contacted with an effective corrosion-inhibiting amount of one or more of these compounds. "Metal surfaces" which may be protected by the corrosion inhibition properties of the compounds of the present invention include ferrous and non-ferrous metals such as cast iron, steel, brass, copper, solder, aluminum, and other materials commonly used with corrosive liquids. It is understood that the term "effective corrosion-inhibiting amount" as used in the specification and claims herein is intended to include any amount that will prevent or control the corrosion on said metal surfaces. Of course, this amount may be constantly changing because of the possible variations in many parameters. Some of these parameters may include the specific corrosive material present; the specific compounds used; the specific metal to be protected against corrosion; the salt and oxygen content in the system; the geometry and capacity of the system to be protected against corrosion; flow velocity of the corrosive material; temperature and the like.

One preferred use of the corrosion inhibitors of the present invention is in aqueous acidic solutions or baths which are in contact with metal surfaces. Such acidic solutions include mineral acid solutions such as sulfuric acid, hydrochloric acid, or the like. These acidic solutions may be used for acid-pickling baths for the surface cleaning of metals or in similar processes. The preferred amount of this corrosion inhibitor in such acid solutions is preferably at least 0.005% by weight of the solution; more preferably, from about 0.01% to about 0.5% by weight of the solution or bath.

Acid pickling solutions or baths are commonly used to remove rust or scale from the surfaces of metals. In commercial operations, this rust or scale is removed by immersing a metal sheet, plate, bar, or the like in the acid pickling solution. The acid solution attacks and dissolves the rust or scale. Once the scale is dissolved, the acid is then free to further attack the metal surface. In order to reduce this attack on the metal, corrosion inhibitors are added to the pickling acid solution.

Another preferred use of the corrosion inhibitors is in aqueous salt solutions such as brines and sour brines. These brines and sour brines may be encountered in oil drilling or the like. The preferred amount of the corrosion inhibitors of the present invention in these types of applications is from about 5 ppm to about 1000 ppm by weight of the salt solution; more preferably, from about 25 ppm to about 100 ppm by weight of the salt solution.

The compounds of this invention may be used for other corrosion protection applications beside the above-mentioned preferred applications. In addition, these compounds may be employed with other known corrosion inhibitors and/or with inert substances such as fillers, dispersing agents, and the like.

The following examples further illustrate the present invention. All parts and percentages employed herein are by weight unless otherwise indicated.

EXAMPLE 1

Reaction Product of POCl$_3$ with N$_2$H$_4$.6PO (containing HCl)

The six mole propylene oxide (PO) adduct of hydrazine (N$_2$H$_4$.6PO) [230.0 grams (0.614 moles)] was charged into a 500 ml round bottom flask. Phosphoryl chloride (POCl$_3$) [31.80 grams (0.205 moles)] was then added slowly with vigorous stirring over a period of three hours. The temperature of the reaction mixture was observed to increase during the initial stages of the reaction, and the color of the mixture darkened from pale yellow to light orange. After the POCl$_3$ addition was complete, the reaction mixture was heated to 70° C.–80° C. under vacuum for an additional two hours, giving a quantitative yield of a brown resinous product, referred to in the Tables below as Compound I. By chloride analysis and NMR analysis, it was determined that the product contained bound HCl, which is also produced in the course of this reaction.

EXAMPLE 2

Reaction Product of PSCl$_3$ with N$_2$H$_4$.6PO (containing HCl)

The procedure of Example 1 was repeated except the amount of N$_2$H$_4$.6PO charged was decreased [180.0 grams (0.481 moles)] and thiophosphoryl chloride (PSCl$_3$) [27.14 grams (0.160 moles)] was employed instead of the POCl$_3$. This reaction gave a quantitive yield of a brown resinous product, referred to in the Tables below as Compound II. By chloride analysis, it was determined that the product contained bound HCl, which was also produced during this reaction.

EXAMPLE 3

Reaction Product of POCl$_3$ with N$_2$H$_4$.12PO (containing HCl)

The procedure of Example 1 was repeated except the twelve mole propylene oxide (PO) adduct of hydrazine (N$_2$H$_4$.12PO) [226.3 grams (0.311 moles)] and POCl$_3$ [16.45 grams (0.106 moles)] were charged. This reaction gave a brown viscous liquid, referred to in the Tables below as Compound III. By chloride analysis, it was determined that the product contained bound HCl, which was also produced during this reaction.

EXAMPLE 4

Reaction Product of PSCl$_3$ with N$_2$H$_4$.12PO (containing HCl)

The procedure of Example 3 was repeated except the amount of N$_2$H$_4$.12PO charged was decreased [135.8 grams (0.187 mole)] and thiophosphoryl chloride (PSCl$_3$) [10.55 grams (0.0622 moles)] was employed instead of POCl$_3$. This reaction gave a quantitive yield of a brown viscous liquid, referred to in the Tables below as Compound IV. By chloride analysis, it was determined that the product contained bound HCl, which was also produced during this reaction.

EXAMPLE 5

Reaction Product of POCl$_3$ with N$_2$H$_4$.20PO (containing HCl)

The procedure of Example 1 was repeated except the twenty mole propylene oxide (PO) adduct of hydrazine (N$_2$H$_4$.20PO) [263.2 grams (0.221 mole)] and POCl$_3$ [11.42 grams (0.0744 mole)] were charged. This reaction gave a brown viscous liquid, referred to in the Tables below as Compound V. By chloride analysis and NMR analysis, it was determined that the product contained bound HCl, which was also produced during this reaction.

EXAMPLE 6

Reaction Product of PSCl$_3$ with N$_2$H$_4$.20PO (containing HCl)

The procedure of Example 5 was repeated except the amount of N$_2$H$_4$.20PO charged was changed [263.78 grams (0.221 mole)] and PSCl$_3$ [12.50 grams (0.0738 moles)] was employed instead of POCl$_3$. This reaction gave a quantitive yield of a brown viscous liquid, referred to in the Tables below as Compound VI. By chloride analysis, it was determined that the product contained bound HCl, which was also produced during this reaction.

EXAMPLES 7–10

As mentioned, the above-made products contain bound HCl. Samples of Compounds I–IV were dissolved in distilled water to make 50% by weight solutions. These aqueous solutions were individually passed through an Amberlite IRA-400 (OH) ion exchange resin (approximately 50 cm long and 1 cm in diameter) made by the Rohm and Haas Company of Philadelphia, PA. After passing through the ion exchange resins, the water was stripped off by vaccuum. This procedure removes essentially all of the bound HCl in the compounds. These HCl-free products are referred to as Compounds VII, VIII, IX and X in the Tables below and correspond, respectively, to HCl-free Compounds I to IV.

EXAMPLES 11–13

Samples of the HCl-free Compounds VIII, IX and X were dissolved in water to prepare 50% by weight aqueous solutions. Sufficient hydriodic acid (HI) was added to each of these samples such that, after the vacuum removal of the water, the iodide content of the resulting HI-containing compounds was about 9% by weight. These HI-containing compounds are referred to as Compounds XI, XII and XIII in the Tables below and correspond respectively to HI-containing Compounds VIII, IX and X.

EXAMPLES 14

It was further discovered that the mole ratio of phosphorylation agent to propylene oxide adduct of hydrazine does not have to be 1:3 as in the above syntheses. Thus, the apparatus and procedure of Example 5 were repeated except that the amount of N$_2$H$_4$.20PO charged was changed [199.13 grams, (0.167 moles)] and proportionally less POCl$_3$ was used [5.17 grams, (0.0333 moles)] on a mole basis. This reaction gave a quantitative yield of a brown viscous liquid, referred to in the Tables below as Compound XIV.

EXAMPLE 15

The procedure and apparatus of Example 3 was repeated except that the amount of N$_2$H$_4$.12PO charged was changed [264.21 grams, (0.362 moles)] and proportionally more POCl$_3$ was used [28.15 grams, (0.181 moles)] on a molar basis. This reaction gave a quantitative yield of a viscous brown liquid, referred to in the Tables below as Compound XV.

EXAMPLE 16

Example 15 was repeated except that the amount of N$_2$H$_4$.12PO charged was changed [195.69 grams, (0.268 moles)] and PSCl$_3$ was used [22.74 grams, (0.134 moles)]. This reaction yielded quantitatively a brown viscous liquid referred to in the Tables below as Compound XVI.

EXAMPLE 17

Linear Polarization Method For Testing As Corrosion Inhibitors

Compounds I–XVI, as made above, were tested as corrosion inhibitors in aqueous acidic solutions according to the linear polarization method described in ASTM test method G5-72. The results of this test are given below in Table I.

By this method, the effectiveness of these compounds as corrosion inhibitors was assessed by, first, determining the linear polarization of a mild steel sample in an uninhibited 1.0 N H₂SO₄ solution, and second, in the same 1.0 N H₂SO₄ solution after one of the compounds I to XVI was added (the amount of each compound added was equivalent to 50 parts per million parts by weight of the solution). From these linear polarization measurements, the % protection afforded by each inhibitor in this acid solution was determined by the following formula:

$$\% \text{ Protection} = \frac{LP_u - LP_i}{LP_u} \times 100$$

wherein $LP_u$ is the linear polarization of the uninhibited sample and $LP_i$ is the linear polarization of the sample placed in the acid solution containing the inhibitor compound.

As can be seen from Table I, the various POCl₃ and PSCl₃ adducts of N₂H₄.nPO compounds are better than the corresponding N₂H₄.nPO compounds themselves.

TABLE I

LINEAR POLARIZATION RESULTS
INHIBITOR CONCENTRATION = 50 ppm

| Compound | % Protection in 1.0 N H₂SO₄ |
|---|---|
| I | 90.8 |
| II | 92.9 |
| III | 91.8 |
| IV | 90.7 |
| V | 93.2 |
| VI | 94.1 |
| VII | 87.9 |
| VIII | 93.5 |
| IX | 93.0 |
| X | 93.1 |
| XI | 95.9 |
| XII | 91.9 |
| XIII | 93.8 |
| XIV | 81.6 |
| XV | 93.9 |
| XVI | 91.6 |
| N₂H₄.6PO | 42.8 |
| N₂H₄.12PO | 84.7 |
| N₂H₄.20PO | 80.6 |
| HI | −21.9 |
| N₂H₄.6PO: HI (5:1 Weight Ratio) | 31.2 |

EXAMPLE 18

Testing As Corrosion Inhibitors In Aqueous Acidic Solutions

Some of the Compounds I–XVI were further tested as corrosion inhibitors in the following manner.

Sections of oil well drilling pipe made of J-55 mild steel were used as test coupons. The coupons were each approximately 32 mm × 32 mm × 6 mm with two 4 mm holes drilled in them. The test coupons were degreased with toluene and then with acetone, cleaned in inhibited HCl as described in NACE Standard Test Method 01-69; "Laboratory Corrosion Testing of Metals for the Process Industries". The coupons were rinsed in deionized water and then in acetone. The coupons were finally weighed to the nearest 0.01 gram.

The coupons were immersed in 100 ml of an aqueous 10% H₂SO₄ solution which contained the appropriate amount of inhibitor to be tested. Then, the glass jars each containing a coupon, acid solution and inhibitor were immersed in an oil bath at 92° C. for 6 hours. A glass jar containing coupon and acid but no inhibitor was also immersed at the same time so that uninhibited corrosion rates could be determined for comparison. At the end of this time, the coupons were washed with water, scrubbed, and their physical appearance noted. Next, the coupons were cleaned in inhibited acid, washed with water and then acetone, dried, reweighed and discarded. Duplicates were run in all cases and average values are reported.

The corrosion rates were calculated in pounds/square foot/day and percent protection was calculated using the formula:

$$\% \text{ Protection} = \frac{CR_u - CR_i}{CR_u} \times 100$$

wherein $CR_u$ = corrosion rate of uninhibited sample and $CR_i$ = corrosion rate of inhibited sample. For the present testing, the uninhibited corrosion rates were typically 1.60±0.15 lb/sq ft/day The results of this testing are shown in Table II below. As can be seen the corrosion rates of coupons protected by the present inhibitors are less than coupons left unprotected by any inhibitors. The compounds giving the best % protection were Compounds XI and XIII.

TABLE II

HOT ACID CORROSION TEST RESULTS IN 10%
H₂SO₄ at 92° C.
INHIBITOR CONCENTRATION = 0.25%
BY WEIGHT OF ACIDIC SOLUTION

| Compound | Corrosion Rate (lb/sq ft/day) | % Protection |
|---|---|---|
| IV | 1.53 | 8.2 |
| VIII | 0.34 | 78.6 |
| X | 1.43 | 13.0 |
| XII | 0.14 | 91.5 |
| XIII | 0.09 | 94.1 |
| N₂H₄.6PO | 1.41 | 3.6 |
| N₂H₄.12PO | 1.47 | 0.0 |
| N₂H₄.6PO:HI (5:1 Weight Ratio) | 0.73 | 54.1 |
| HI | 1.30 | 2.3 |

EXAMPLE 19

Testing As Corrosion Inhibitors In Sour Brines

Some of Compounds I-XVI were further tested as corrosion inhibitors for sour brines using the Method described in NACE Publication 1K155 entitled "Proposed Laboratory Standard for Screening Corrosion Inhibitors for Use in Oil and Gas Wells."

By this method, a clean 1"×1"×1/16" mild steel (1010) coupon with a 5/32" drilled hole is suspended for seven days in 900 ml of 5% NaCl in which 500±100 ppm H₂S have been dissolved. Kerosene (100 ml) previously filtered through Fuller's earth floats on top of the brine throughout the test, constituting an oil phase. Inhibitor candidates were tested at 25 ppm and 100 ppm, and corrosion rates in mils per year (mpy) were calculated, as were percent protections, using the formula described in Example 18. Duplicate tests were run for all inhibitors at all concentrations, as were duplicate uninhibited samples. In Table III results of this test are presented.

TABLE III

SOUR BRINE CORROSION TEST RESULTS
INHIBITOR CONCENTRATION = 25 ppm

| Compound | Corrosion Rate (mpy)* | % Protection |
|---|---|---|
| I | 0.768 | 83.6 |
| II | 0.457 | 90.2 |
| III | 0.804 | 83.9 |
| V | 0.284 | 93.9 |
| VI | 0.777 | 85.1 |
| XIV | 2.39 | 63.2 |
| XV | 0.492 | 92.4 |
| XVI | 0.201 | 96.8 |

*Typical uninhibited corrosion rate = 5.5 mpy

What is claimed is:

1. A composition comprising the reaction product of a poly(oxyalkylated) hydrazine and at least one compound selected from the group consisting of a phosphorylating agent, a thiophosphorylating agent, and mixtures thereof, wherein said poly(oxyalkylated) hydrazine has the formula:

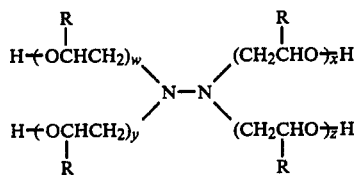

wherein each R is individually selected from hydrogen, lower alkyl groups having from 1 to 4 carbon atoms and phenyl; and the sum of w, x, y, and z is from about 4 to about 25, and wherein the mole ratio of said poly(oxyalkylated) hydrazine to said compound being from about 0.1:1 to 10:1.

2. The composition of claim 1 wherein said phosphorylation agent is selected from the group consisting of phosphoryl chloride, phosphorous pentoxide and mixtures thereof.

3. The composition of claim 1 wherein said thiophosphorylation agent is selected from the group consisting of thiophosphoryl chloride, phosphorous pentasulfide and mixtures thereof.

4. The composition of claim 1 wherein the sum of w, x, y and z is from about 6 to about 20.

5. The composition of claim 1 wherein R is always a hydrogen or a methyl group.

6. The composition of claim 5 wherein said mole ratio is from about 1:1 to about 6:1.

7. The composition of claim 6 wherein said compound is phosphoryl chloride.

8. The composition of claim 6 wherein said compound is thiophosphoryl chloride.

9. A composition comprising the substantially HCl-free reaction product of a poly(oxyalkylated) hydrazine and at least one compound selected from the group consisting of phosphoryl chloride, thiophosphoryl chloride, and mixtures thereof, wherein said poly(oxyalkylated) hydrazine has the formula:

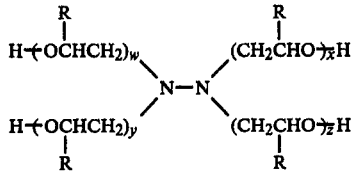

wherein each R is individually selected from hydrogen, lower alkyl groups having from 1 to 4 carbon atoms and phenyl; and the sum of w, x, y, and z is from about 4 to about 25, and wherein the mole ratio of said poly(oxyalkylated) hydrazine to said compound being from about 0.1:1 to about 10:1.

10. The composition of claim 9 wherein said compound is phosphoryl chloride.

11. The composition of claim 9 wherein said compound is thiophosphoryl chloride.

12. The composition of claim 9 wherein said mole ratio is from about 1:1 to about 6:1.

13. A composition comprising an adduct of an iodide-containing compound and a reaction product of a poly(oxyalkylated) hydrazine and at least one compound selected from the group consisting of a phosphorylation agent, a thiophosphorylation agent and mixtures thereof, wherein said poly(oxyalkylated) hydrazine has the formula:

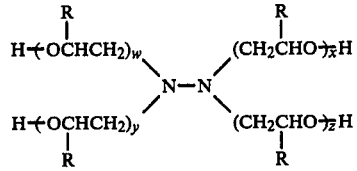

wherein each R is individually selected from hydrogen, lower alkyl groups having from 1 to 4 carbon atoms and phenyl; and the sum of w, x, y, and z is from about 4 to about 25, and wherein the mole ratio of said poly(oxyalkylated) hydrazine to said compound being from about 0.1:1 to about 10:1.

14. The composition of claim 13 wherein said iodide-containing compound is hydrogen iodide.

15. The composition of claim 13 wherein said compound is phosphoryl chloride.

16. The composition of claim 14 wherein said compound is thiophosphoryl chloride.

17. An acid metal-treating bath comprising an acid and an effective corrosion-inhibiting amount of a composition of claim 1.

18. The acid bath of claim 17 wherein the acid comprises sulfuric acid or hydrochloric acid.

19. An acid metal-treating bath comprising an acid and an effective corrosion-inhibiting amount of a composition of claim 9.

20. An acid metal-treating bath comprising an acid and an effective corrosion-inhibiting amount of a composition of claim 13.

21. A process of inhibiting the corrosion of metals which come into contact with an acid solution, which comprises contacting the surface of the metal to be inhibited against corrosion with the corrosion-inhibited acid metal-treating bath of claim 17.

22. The process of claim 21 wherein the acid in said acid bath comprises sulfuric acid or hydrochloric acid.

23. A process of inhibiting the corrosion of metals which come into contact with an acid solution, which comprises contacting the surface of the metal to be inhibited against corrosion with the corrosion-inhibited acid metal-treating bath of claim 19.

24. A process of inhibiting the corrosion of metals which come into contact with an acid solution, which comprises contacting the surface of the metal to be inhibited against corrosion with the corrosion-inhibited acid metal-treating bath of claim 20.

25. A brine-containing solution comprising a brine and an effective corrosion-inhibiting amount of a composition of claim 1.

26. A brine-containing solution comprising a brine and an effective corrosion-inhibiting amount of a composition of claim 9.

27. A brine-containing solution comprising a brine and an effective corrosion-inhibiting amount of a composition of claim 13.

28. A process of inhibiting the corrosion of metals which come into contact with a brine solution, which comprises contacting the surface of the metal to be inhibited against corrosion with the corrosion-inhibited brine solution of claim 25.

29. A process of inhibiting the corrosion of metals which come into contact with a brine solution, which comprises contacting the surface of the metal to be inhibited against corrosion with the corrosion-inhibited brine solution of claim 26.

30. A process of inhibiting the corrosion of metals which come into contact with a brine solution, which comprises contacting the surface of the metal to be inhibited against corrosion with the corrosion-inhibited brine solution of claim 27.

31. A process for inhibiting corrosion of metal surfaces caused by corrosive aqueous solutions, which comprises contacting said metal surfaces with an effective corrosion-inhibiting amount of a composition of claim 1.

32. A process for inhibiting corrosion of metal surfaces caused by corrosive aqueous solutions, which comprises contacting said metal surfaces with an effective corrosion-inhibiting amount of a composition of claim 9.

33. A process for inhibiting corrosion of metal surfaces caused by corrosive aqueous solutions, which comprises contacting said metal surfaces with an effective corrosion-inhibiting amount of a composition of claim 13.

* * * * *